United States Patent [19]

Gittleman

[11] Patent Number: 4,657,510
[45] Date of Patent: Apr. 14, 1987

[54] HYBRID DENTAL IMPLANT SYSTEM

[75] Inventor: Neal B. Gittleman, Houston, Tex.

[73] Assignee: Implant Systems, Inc., Philadelphia, Pa.

[21] Appl. No.: 708,875

[22] Filed: Mar. 6, 1985

[51] Int. Cl.⁴ .............................................. A61C 8/00
[52] U.S. Cl. ..................................... 433/173; 433/174
[58] Field of Search ................ 433/173, 174, 175, 176

[56] References Cited

U.S. PATENT DOCUMENTS

| | | | |
|---|---|---|---|
| 3,589,011 | 6/1971 | Sneer | 433/174 |
| 3,955,280 | 5/1976 | Sneer | 433/176 |
| 4,488,875 | 12/1984 | Niznick | 433/173 |
| 4,552,532 | 11/1985 | Mozsary | 433/173 |

*Primary Examiner*—Robert Peshock
*Attorney, Agent, or Firm*—Lerner, David, Littenberg, Krumholz & Mentlik

[57] ABSTRACT

A hybrid dental implant system is described and illustrated, which provides the dental profession with an implant system having a built-in contingency option by being able to go from a fixed implant modality to a retentive nonstress bearing removable one. The implant system includes a sleeve member adapted to be surgically inserted into the jawbone of a patient for alternatively receiving a fixed implant member or retentive implant member. The fixed implant member having a stress breaking device, is designed for supporting a crown and bridge prosthesis. The retentive implant member having an inciso-apically movable insert allows the underside of a denture to exert occlusal and masticatory forces upon the underlying soft gum tissue, thereby dissipating such forces before they are transmitted to the implant itself. Should an abutment tooth anterior or posterior to a fixed implant fail, the fixed implant member is simply screwed out of its retaining sleeve member and a retentive implant member is screwed into its place for retaining a full or partial denture.

12 Claims, 7 Drawing Figures

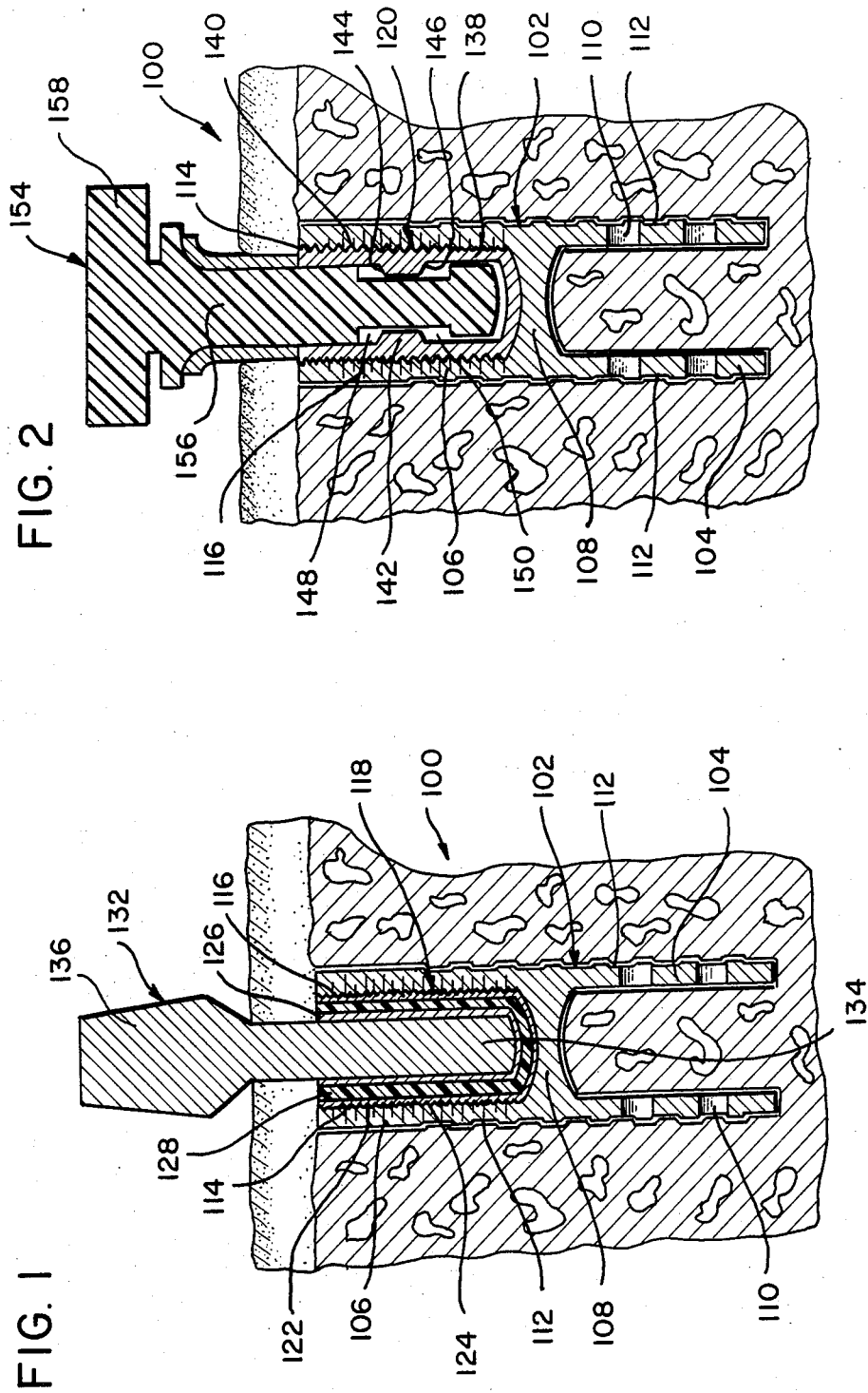

HYBRID DENTAL IMPLANT SYSTEM

BACKGROUND OF THE INVENTION

The present invention relates in general to a hybrid dental implant system and more particularly, to such a hybrid dental implant system constructed and arranged to facilitate the recreation of a dentition in patients by possessing the ability to freely interconvert from both a fixed and retentive (nonstress bearing) implant modality.

During mastication, teeth are subjected to an infinite number for foce vectors. Most of these forces are directed in an incisio-apical direction, i.e., cusp tip to root tip, but some forces are directed the other way, i.e., apico-incisal. These latter forces tend to dislodge full and removable partial dentures, thereby presenting a continual problem to the patient and dentist. In this regard, dental implants were created to help the dentist most naturally recreate a dentition in patients who had lost some or all of their teeth. These implants, in specific cases, have superseded full and removable partial dentures. The dental implant disclosed is an endosseous basket placed into a surgically prepared site in the jawbone. A prosthesis is then attached to that portion of the implant that extends through the soft gum tissue into the patient's mouth. One such dental implant is illustrated in U.S. Pat. No. 4,359,318 in the name of Neal Gittleman.

In general, these implants have been constructed in a variety of forms for use by the dentist, either as a fixed implant or as a retentive implant. The fixed implant, used for crown and bridge support, is generally preferred by dentists as it aids in restoring a more natural dentition. In the dentate patient chewing forces are absorbed in part by the resilient action of the bone and periodontal ligament, while a fixed implant loads the bone directly.

The retentive implant, on the other hand, is designed to retain a prosthesis, not support it as in the case of the fixed implant. The retentive design prevents dislodgement of the prosthesis when it is subjected to apico-incisal forces, yet minimizes the occlusal forces placed upon the implant by allowing the soft gum tissue to absorb most of the inciso-apical forces. The retentive implant combines the desirable aspects of full and removable partial dentures with those of an endosseous fixed dental implant. For example, the retentive implant overcomes the problem encountered with full and removable partial dentures by resisting dislodging forces. The prosthesis, connected to the jawbone via the implant, has a limited movement when subjected to apico-incisal forces. As a result, forces which can cause movement of the implant within bone will be maintained. This will manifest itself in a lower rate of peri-implant epithelialization, peri-implant infection, and implant failure.

In the event of failure of a fixed implant and/or natural abutment, it is often desirable that a retentive implant securing a denture be utilized. Furthermore, fixed implant modalities often do not lend themselves to be easily converted for use as a retentive implant. Therefore, it may be required that the dentist remove the prosthesis and fixed implant, in order that a retentive modality be substituted for retaining a full or partial denture. This procedure may subject both the patient and dentist to increased chair time, additional surgery, and further expenses.

SUMMARY OF THE INVENTION

It is broadly an object of the present invention to provide a hybrid dental implant system which overcomes or avoids one or more of the foregoing disadvantages resulting from the use of the above-mentioned prior art dental implants, and which fulfills the specific requirement of such a hybrid dental implant system possessing the ability to go from a fixed implant modality to a retentive, nonstress bearing removable implant modality. Specifically, it is within the contemplation of one aspect of the present invention to provide a hybrid dental implant system which, should an abutment tooth anterior or posterior to a fixed implant fail, a fitting can be simply screwed out of an endosseous basket and a retentive fitting screwed into the basket in its place.

Another object of the present invention is to provide a hybrid dental implant system, which when employing a retentive implant, is virtually stress-free by minimizing the occlusal forces that are placed on the implant.

Another object of the present invention is to provide a hybrid dental implant system, which when employing a retentive implant, provides increased masticatory efficiency, and subjectively, the feeling of having a more functional and asthetic dentition.

Another object of the present invention is to provide a hybrid dental implant system, which when employing a retentive implant, combines the best aspects of full and removable partial dentures with that of an endosseous fixed dental implant.

Another object of the present invention is to provide a hybrid dental implant system, which when employing a retentive dental implant, has its fulcrum point beneath cortical bone.

Another object of the present invention is to provide a hybrid dental implant system, which when employing a retentive dental implant, reduces the lever arm of the implant upon loading by virtue of the implant being constructed of resilient material and the location of its fulcrum point.

Another object of the present invention is to provide a hybrid dental implant system, which when employing a fixed implant will predictably support an occlusion.

Another object of the present invention is to provide a hybrid dental implant system, which when employing a fixed implant, incorporates a stress breaking device in the nature of an artificial periodontal ligament.

Another object of the present invention is to provide a hybrid dental implant system, which when employing a fixed implant, includes a stress breaking device which is substantially isolated from the cortical bone and soft gum tissue.

Another object of the present invention is to provide a hybrid dental implant system which avoids inflammation, infection and hard tissue resorption.

Another object of the present invention is to provide a hybrid dental implant system which is permanently anchored in the jawbone through bone growth.

In accordance with one embodiment of the present invention, there is provided a dental implant system for attaching a dental prosthesis to a jawbone underlying gum tissue. The dental implant system is constructed of a sleeve member to be secured within an upper portion of the jawbone, fixed implant means to be received by the sleeve for securing a dental prosthesis thereto, and retentive implant means to be alternatively received by the sleeve member for retaining the dental prosthesis while the prosthesis is at least partially supported by gum tissue.

BRIEF DESCRIPTION OF THE DRAWINGS

The above description, as well as further objects, features and advantages of the present invention will be more fully understood by reference to the following detailed description of a presently preferred, but nonetheless illustrative, hybrid dental implant system in accordance with the present invention when taken in conjunction with the accompanying drawings, wherein:

FIG. 1 is a cross-sectional view of the hybrid dental implant system employing an endosseous basket and a fixed implant member, including a stress breaking device;

FIG. 2 is a cross-sectional view of the hybrid dental implant system as shown in FIG. 1 employing an endosseous basket and a retentive implant member adapted to allow a dental prosthesis to be supported on gum tissue;

DETAILED DESCRIPTION

Figure 3:
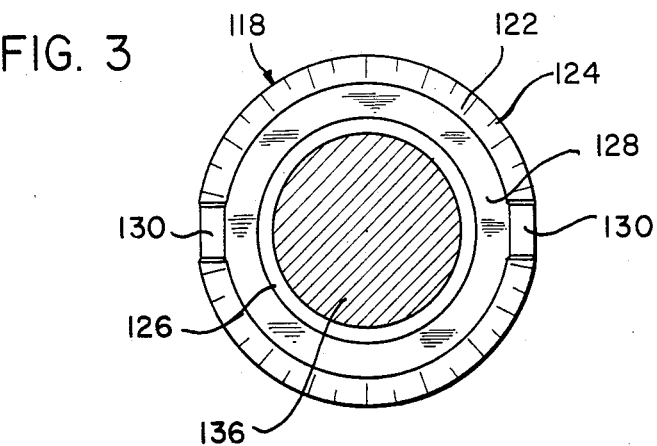
FIG. 3 is a top plan view of the fixed implant member as shown in FIG. 1.

Referring now to the drawings, wherein like reference numerals represent like elements, there is disclosed in FIGS. 1 and 2 a hybrid dental implant system generally designated by reference numeral 100. The implant system 100 includes a sleeve member 102 which is preferably constructed from surgical titanium or alternatively a ceramic or possibly one of the hydroxylapatite materials. The sleeve member 102 includes a hollow cylindrical lower portion 104 and a hollow cylindrical upper portion 106 separated from the lower portion by rib 108. A series of apertures 110 are provided about the lower portion 104, while a plurality of grooves 112 are provided circumscribing the sleeve member 102 as to be described hereinafter. The upper portion 106 is provided with a central bore 114 extending to the rib 108 and provided with a plurality of internal threads 116. In accordance with one embodiment, the sleeve member 102 has an overall length of about 12 millimeters and an outside diameter of about 4 millimeters.

Figure 4:
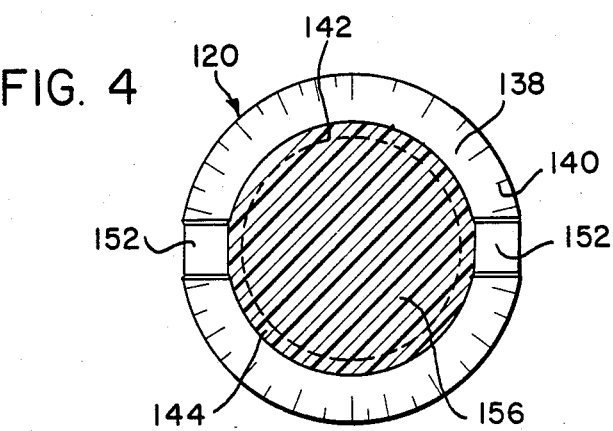
FIG. 4 is a top plan view of the retentive implant member as shown in FIG. 2.

The implant system 100 includes a fixed implant member 118, as shown in cross-section in FIG. 1 and in plan view in FIG. 3; and a retentive implant member 120, as shown in cross-section in FIG. 2 and in plan view in FIG. 4. Referring now to FIGS. 1 and 3, the fixed implant member 118 includes a cylindrical hollow outer core 122 having a closed end and a plurality of external threads 124, a concentrically arranged inner sleeve 126 having a closed end 127 and providing a surrounding annular opening between the core and inner sleeve, and a spacer 128 of resilient material, for example, silicon, provided within the annular opening.

The hollow core 122 is provided at its upper edge with a pair of spaced-apart notches 130 as to be described hereinafter. The hollow core 122 and inner sleeve 126 are preferably constructed from surgical titanium. In accordance with one embodiment, the fixed implant member 118 has an overall length of about 6 millimeters and an outside diameter of about 3 millimeters. The fixed implant member 118 is adapted to be threadedly received within the threaded core 114 in the upper portion 106 of the sleeve member 102. A fixed implant insert 132 constructed of surgical titanium, includes an elongated cylindrical stem 134 adapted to be slidingly received within the inner sleeve 126 of the fixed implant member 118 and an enlarged head 136. Although they fixed implant insert 132 has been described as a cylindrical member, it is to be understood that the fixed implant insert may be constructed in the form of a flat blade and the like.

Referring now to FIGS. 2 and 4, the retentive implant member 120 includes a cylindrical hollow core 138 of surgical titanium and having a closed end 139 and a plurality of external threads 140. A retentive lip 142 formed between a pair of cam surfaces 144, 146 is arranged extending inwardly from the interior surface of the inner sleeve 126. The retentive lip 142 is constructed in the form of a circular ring arranged at a location approximately 3 millimeters along the length of the inner sleeve 126 and dividing the inner sleeve into an upper hollow region 148 and a lower hollow region 150. The inner sleeve 126, in one embodiment, has an overall length of about 6 millimeters and an outside diameter of about 3 millimeters. A pair of opposed spaced-apart notches 152 are provided within the upper edge of the inner sleeve 126 in the manner of notches 130 provided within the upper edge of the hollow core 122 of the fixed implant member 118. The retentive implant member 120 is adapted to be threadingly received within the bore 114 of the upper portion 106 of the sleeve member 102, in a similar manner as the fixed implant member 118. That is, the fixed implant member 118 and retentive implant member 120 can be alternatively threadingly received within the bore 114 of the sleeve member 102 as desired.

Accompanying the retentive implant member 120 is a retentive implant insert 154 constructed of an elongated cylindrical stem 156 having an enlarged head 158. The stem 156 has a diameter slightly smaller than the inside diameter of the core 138 to provide smooth sliding engagement therebetween. As shown, the stem 156 includes a section 160 of reduced diameter to provide a longitudinally extending circumscribing channel 162 adapted to receive the retentive lip 142. The channel 162 permits the retentive implant insert 154 to slide longitudinally within the hollow core 138 of the retentive implant member 120 in the order of 1 to 2 millimeters inciso-apically. The retentive implant insert 154 is retained within the core 138 by the lower portion 164 of the stem 156 being retained by its engagement at ridge 165 with the cam surface 146 of the retentive lip 142 under normal occlusal and masticatory forces.

Figure 5:
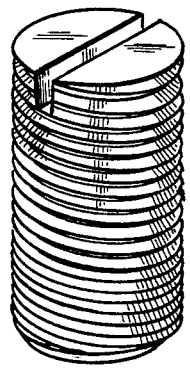
FIG. 5 is a perspective view of an inert biocompatible submergible dowel adapted for use with the endosseous basket as shown in FIGS. 1 and 2.

The jawbone 166, i.e., cortical bone, is prepared for receiving the implant system 100 in the manner disclosed in U.S. Pat. No. 4,359,318. Briefly, a drill (not shown) makes two different cuts in the jawbone 166. Specifically, the drill forms an annular cut 168 which defines the upwardly extending stump 170 and a central opening 172, the annular cut and central opening having a plurality of circumscribing grooves 174. To insert the sleeve member 102 into the jawbone 166 after it has been prepared as shown and described, the sleeve member is lowered into the jawbone so that the lower portion 104 enters the annular cut 168 and the rib 108 is supported by the stump 170. After the sleeve member 102 has been introduced into the surgical site, an inert biocompatible submergible dowel, as shown in FIG. 5, is placed within the upper portion 106 of the sleeve member. The dowel 176 includes a plurality of external threads 178 and a slot 180 extending within its upper surface 182. The dowel 176 is threadingly received within the sleeve member 102 using a screwdriver engaging the slot 180 or other such implement. However, the dowel 176 can be constructed without threads 178 and secured within the sleeve member 102 using a temporary cementing agent. The dowel 176 prevents the down-growth of soft gum tissue 184 within the upper portion 106 of the sleeve member 102 while the jawbone 166 heals.

The sleeve member 102 is retained within the jawbone 166 and buried beneath the gum tissue 184 for a period of three to six months, and left undisturbed to allow for complete healing. In this regard, healing can be promoted by application of an electric current in the manner disclosed in the aforesaid patent. It will be appreciated that the sleeve member 102 will provide an unusually strong bond with the jawbone 166, once the bone has knit through the apertures 110. In addition, the grooves 112, being dimensioned approximately one-third of a millimeter in height and one-quarter of a millimeter in depth, facilitates the securing of a sleeve member 102 within the jawbone 166. The grooves 112 along with the apertures 110, allow the jawbone 166 to mechanically interlock the sleeve member 102 in a manner known as osseointergration. Once the jawbone 166 has healed, as determined radiologically, so as to secure the sleeve member 102 therein, the gum tissue 184 is opened and the dowel 176 removed. In its place either the fixed implant member 118 or retentive implant member 120 is threadingly received within the upper portion 106 of the sleeve member 102 for the purpose as now to be described.

Figure 6:
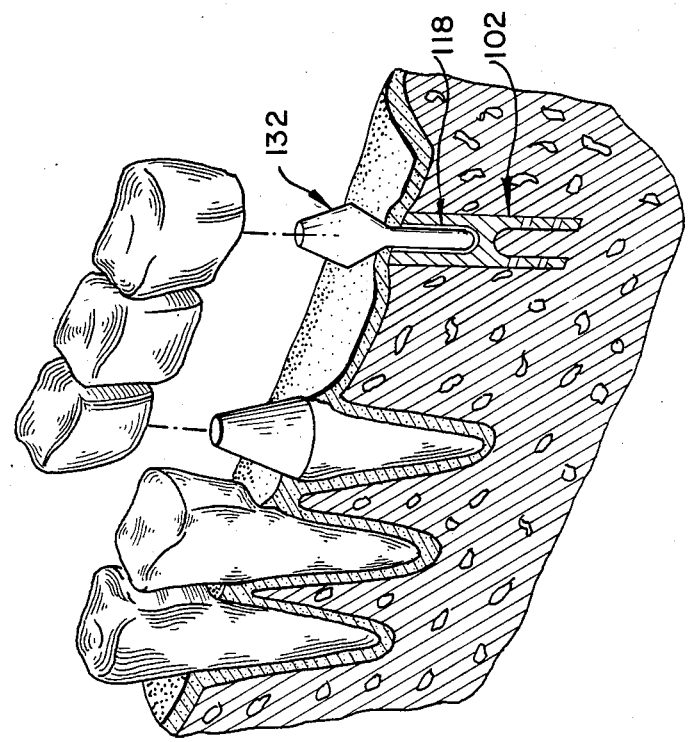
FIG. 6 is a front elevational view, in partial cross-section, showing the use of a fixed implant member for supporting a crown and bridge prosthesis.

Referring to FIG. 6, there is shown a portion of a patient's mouth having three anterior teeth 186, 188, 190 supported within the jawbone 166 by periodontal ligaments 192. Tooth 190 is prepared at location 193 in a conventional manner as an abutment tooth for receiving a crown and bridge prosthesis 194. A sleeve member 102 of the hybrid dental implant system 100 of the present invention is inserted into the jawbone 166 in the manner as thus far described. A fixed implant member 118 is threadingly received within the upper portion 106 of the sleeve member 102 using a screwdriver engaging the notches 130. A fixed implant insert 132 is secured within the inner sleeve 126 of the fixed implant member 118, such that head 136 extends above the gum tissue 184. The fixed implant insert 132 functions as an abutment for receiving the crown and bridge prosthesis 194. The crown and bridge prosthesis 194 is secured to the abutment tooth 190 and to the head 136 of the fixed implant insert 132 using any suitable means, for example, a screw (not shown) provided within an opening extending through each crown. However, other arrangements may be devised for removably attaching the crown and bridge prosthesis 194 to the abutment tooth 190 and fixed implant insert 132.

The hybrid dental implant system 100, as described with reference to FIG. 6, functions as a fixed implant system for supporting the crown and bridge prosthesis 194 to help the dentist more naturally recreate a dentition in patients who have lost some or all of their teeth. The occlusal and masticatory forces exerted upon the fixed implant 118 are absorbed by the resilient spacer 128, which functions as a stress breaking device, and more specifically, as an artificial periodontal ligament. The resilient spacer 128, unlike the periodontal ligament, is isolated from the jawbone 166 by being provided within the annular space provided between the inner sleeve 126 and hollow core 122 of the fixed implant member 118. Thus, for the first time, a fixed implant system, as sued for supporting a crown and bridge prosthesis 194, is predictable by being able to support an occlusion.

In the event of failure of the crown and bridge prosthesis 194, for example, as a result of gum disease, occlusal trauma, jawbone breakdown, or extraction of an abutment tooth, it is often required that the crown and bridge prosthesis be replaced by a full or partial denture. Previously, it would have been required that the sleeve member 102 be surgically removed and replaced with a suitable implant adapted for retaining a denture. However, the hybrid dental implant system 100 of the present invention avoids the need of having to remove both the failed crown and bridge prosthesis 194 and sleeve member 102 of the fixed implant member 118.

Figure 7:
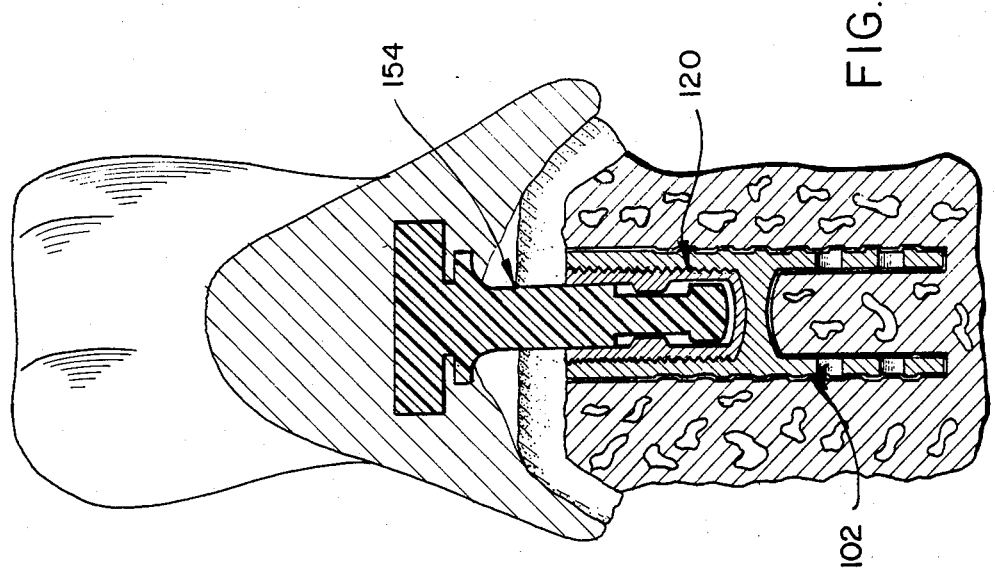
FIG. 7 is a cross-sectional view of the dental hybrid implant system as shown in FIG. 2, illustrating its retention of a denture by a retentive implant member, and which denture is being partially supported by soft gum tissue.

As shown in FIG. 7, after the crown and bridge prosthesis 194 has been removed, the fixed implant member 118 is removed from the upper portion 106 of the sleeve member 102 and replaced with a retentive implant member 120 using a suitable screwdriver engaging notches 152. A cylindrical centering member 196 is positioned about the upper portion of stem 156 of the retentive implant insert 154. The stem 156 is inserted as fully as possible into the hollow core 138 by urging its lower portion 164 past the retentive lip 142, which is accommodated as by the resilient construction of the retentive implant insert 154. As more clearly shown in FIG. 2, the lower portion 164 of the retentive implant insert 154 is retained within the lower region 150 while the retentive lip 142 is captured within the channel 162 provided along the stem 156. The centering member 196 prevents the retentive implant insert 154 from bending when securing a denture to its head 158 using a suitable adhesive, i.e., an acrylic. Specifically, a "pick-up" technique, using a quick setting acrylic adhesive is employed to capture the head 158 of the retentive implant insert 154 on the under surface of a denture 198 which supports a plurality of teeth 200, as shown in FIG. 7. After the acrylic adhesive has set up and hardened, and the capturing process completed, the centering member 196 is discarded. In order to support a full or partial denture 198, a plurality of retentive implant members 120 are provided within sleeve members 102 secured within the jawbone 166 of the patient.

Unlike the fixed implant member 118, the retentive implant member 120 permits the denture 198 to be, for the most part, supported by the underlying gum tissue 184. Thus, occlusal and masticatory forces are mostly distributed to the underlying gum tissue 184, as opposed to being entirely supported by the denture 196 and retentive implant member 120, as would be the case when employing the fixed implant member 118 as shown in FIG. 6. That is, the occlusal and masticatory forces being supported directly by the crown and bridge prosthesis 194, abutment tooth 190 and fixed implant member 118. The retentive implant member 120 prevents dislodgement of the denture 198 when it is subjected to apico-incisal forces, yet minimizes the stresses placed upon the implant by allowing the soft gum tissue 184 to absorb most of the incisal-apico forces. The retentive lip 142 of the retentive implant member 120, being captured within the channel 162 of the fixed implant insert 132, permits sliding movement of up to 1 to 2 millimeters inciso-apically, thereby allowing the underside of the denture 198 to exert force upon the underlying soft gum tissue 184, thereby dissipating it before any such force is transmitted to the implant itself. Should these forces be applied directly to the retentive implant member 120, for example, due to the settling of the denture 194, these forces are minimized due to the retentive implant insert 154 being constructed of flexible resilient material such as nylon. In addition, inciso-apical and apico-incisal forces are minimized by placing the fulcrum point, i.e., the lower portion 164 of the retentive implant insert 154, below the surface of the jawbone 106 within the lower region 150 of the sleeve member 102. That is, by reducing the fulcrum arm, as designated by letter F in FIG. 2, the transmission of these forces to the jawbone 166 and sleeve member 102 is substantially reduced.

As will be readily apparent to those skilled in the art, the invention may be used in other specific forms without departing from its spirit or essential characteristics. The present embodiments are, therefore, to be considered as illustrative and not restrictive, the scope of the invention being indicated by the claims rather than the foregoing description, and all changes which come within the meaning and range of equivalence of the claims are therefore intended to be embraced therein.

I claim:

1. A dental implant system for attaching a dental prosthesis to a jawbone underlying gum tissue, said implant system comprising a sleeve member to be secured within an upper portion of said jawbone, fixed implant means to be received by said sleeve member for securing said prosthesis, said fixed implant means including a fixed implant member received by said sleeve member and a fixed implant insert secured to said prosthesis and received by said fixed implant member to prevent movement of said fixed implant insert along the longitudinal axis of said sleeve member, and retentive implant means to be alternately received by said sleeve member upon removal of said fixed implant means for retaining said prosthesis while said prosthesis is at least partially supported by said gum tissue, said retentive implant means including a retentive implant member received by said sleeve member, and said retentive implant member including a retentive lip arranged circumscribing the interior surface thereof, and a retentive implant insert secured to said dental prosthesis and received by said retentive implant member for retaining said dental prosthesis while said prosthesis is being supported by said gum tissue, said retentive implant insert having a recess larger than said retentive lip for receiving said retentive lip therein to permit movement of said retentive implant insert along the longitudinal axis of said sleeve member.

2. The dental implant system of claim 1 wherein said sleeve member includes a substantially cylindrical upper and lower portion constructed and arranged to be secured within said upper portion of said jawbone.

3. The dental implant system of claim 2 wherein said upper portion of said sleeve member includes a bore adapted to alternatively receive therein said fixed implant means and said retentive implant means.

4. The dental implant system of claim 1 wherein said fixed implant member comprises a hollow core adapted to be received by said sleeve member, a concentrically arranged inner sleeve providing an annular opening between said core and said inner sleeve, and a spacer of resilient material provided within said annular opening.

5. The dental implant system of claim 1 further including means for alternatively securing said fixed implant means and said retentive implant means to said sleeve member.

6. The dental implant system of claim 5 wherein said securing means comprises a plurality of threads provided along a portion of the interior surface of said sleeve member and adapted to engage a plurality of corresponding threads provided on the exterior surface of said fixed implant means and said retentive implant means.

7. The dental implant system of claim 1 further including a cam surface arranged on either side of said retentive lip.

8. The dental implant system of claim 1 wherein the lower portion of said retentive implant insert within the lower region of said retentive implant member provides a fulcrum point for said retentive implant insert at a location below the surface of said jawbone.

9. The dental implant system of claim 1 further including means adapted to be received by said sleeve member for preventing gum tissue growth within said sleeve member during the securing of said sleeve member within said jawbone.

10. The dental implant system of claim 1 wherein said retentive implant insert is constructed of flexible material.

11. A dental implant system for attaching a dental prosthesis to a jawbone underlying gum tissue, said implant system comprising:
(a) a sleeve member to be secured within an upper portion of said jawbone, said sleeve member including a substantially cylindrical upper portion having a bore and a lower portion,
(b) a fixed implant member to be received within said bore for securing a dental prosthesis thereto, said fixed implant member including a substantially cylindrical hollow first core, a concentrically arranged inner sleeve providing an annular opening between said first core and said inner sleeve, a spacer of resilient material provided within said annular opening, and a fixed implant insert to be secured to said inner sleeve and having said dental prosthesis attached thereto,
(c) a retentive implant member to be received within said bore upon removal of said fixed implant member for retaining a dental prosthesis while said prosthesis is at least partially supported by said gum tissue, said retentive implant member including a substantially cylindrical hollow second core, a retentive lip arranged circumscribing the interior surface of said second core to define an upper and lower region therein, and a retentive implant insert secured to a dental prosthesis and removably received within said core, said retentive implant insert including a lower portion having a recess larger than said retentive lip for receiving said retentive lip therein to permit movement of said retentive implant insert within said second core along the longitudinal axis of said sleeve member, said lower portion of said retentive implant insert providing a fulcrum point below the surface of said jawbone, and (d) securing means for alternatively securing said fixed implant member and said retentive implant member within said bore of said sleeve member.

12. The dental implant system of claim 11 wherein said retentive implant insert is constructed of resilient material.

* * * * *

UNITED STATES PATENT AND TRADEMARK OFFICE
CERTIFICATE OF CORRECTION

PATENT NO. : 4,657,510

DATED : April 14, 1987

INVENTOR(S) : Gittleman

It is certified that error appears in the above-identified patent and that said Letters Patent is hereby corrected as shown below:

Column 1:

Line 13, change "for foce" to --of force--;

Line 54, changed "maintained" to --minimized--.

Column 4:

Line 14, change "they" to --the--.

Column 6:

Line 13, change "sued" to --used--.

Column 7:

Line 20, change "106" to --166--.

Signed and Sealed this

Twenty-second Day of September, 1987

Attest:

DONALD J. QUIGG

*Attesting Officer*  *Commissioner of Patents and Trademarks*